United States Patent
Chen et al.

(10) Patent No.: US 10,779,799 B2
(45) Date of Patent: Sep. 22, 2020

(54) METHOD FOR ULTRASOUND ELASTOGRAPHY THROUGH CONTINUOUS VIBRATION OF AN ULTRASOUND TRANSDUCER

(71) Applicant: MAYO FOUNDATION FOR MEDICAL EDUCATION AND RESEARCH, Rochester, MN (US)

(72) Inventors: Shigao Chen, Rochester, MN (US); James Greenleaf, Rochester, MN (US); Daniel C. Mellema, Rochester, MN (US); Pengfei Song, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/522,067

(22) PCT Filed: Oct. 28, 2015

(86) PCT No.: PCT/US2015/057825
§ 371 (c)(1),
(2) Date: Apr. 26, 2017

(87) PCT Pub. No.: WO2016/069750
PCT Pub. Date: May 6, 2016

(65) Prior Publication Data
US 2017/0333005 A1 Nov. 23, 2017

Related U.S. Application Data

(60) Provisional application No. 62/072,167, filed on Oct. 29, 2014.

(51) Int. Cl.
*A61B 8/00* (2006.01)
*A61B 5/00* (2006.01)
(Continued)

(52) U.S. Cl.
CPC ............. *A61B 8/5207* (2013.01); *A61B 8/14* (2013.01); *A61B 8/4444* (2013.01);
(Continued)

(58) Field of Classification Search
CPC ...................................... A61B 8/485
See application file for complete search history.

(56) References Cited

U.S. PATENT DOCUMENTS 5,524,636 A * 6/1996 Sarvazyan ........... A61B 1/0052
600/587
6,329,821 B1 * 12/2001 Zhou ................ G01R 33/56563
324/307
(Continued)

FOREIGN PATENT DOCUMENTS

CN 102151152 A 8/2011
CN 102782518 A 11/2012
(Continued)

OTHER PUBLICATIONS

"On the Effects of Reflected Waves in Transient Shear Wave Elastography" by T. Deffieux et al. IEEE Trans Ultra Ferro Freq Ctrl. vol. 58, No. 10. 2011. pp. 2032-2035.*
(Continued)

*Primary Examiner* — Jeffrey G Hoekstra
*Assistant Examiner* — Jason M Ip
(74) *Attorney, Agent, or Firm* — Quarles & Brady LLP (57) ABSTRACT

A method for imaging an object by ultrasound elastography through continuous vibration of the ultrasound transducer is taught. An actuator directly in contact with the ultrasound transducer continuously vibrates the transducer in an axial direction, inducing shear waves in the tissue and allowing for real-time shear wave imaging. Axial motion of the transducer contaminates the shear wave images of the tissue, and must be suppressed. Therefore, several methods for
(Continued)

correcting for shear wave artifact caused by the motion of the transducer are additionally taught.

14 Claims, 6 Drawing Sheets

(51) Int. Cl.
  *A61B 8/08* (2006.01)
  *G01S 7/52* (2006.01)
  *A61B 8/14* (2006.01)

(52) U.S. Cl.
  CPC ............ *A61B 8/4483* (2013.01); *A61B 8/485* (2013.01); *A61B 8/5269* (2013.01); *A61B 8/5276* (2013.01); *G01S 7/52022* (2013.01); *G01S 7/52042* (2013.01); *G01S 7/52077* (2013.01); *A61B 5/0051* (2013.01)

(56) References Cited

U.S. PATENT DOCUMENTS

| | | | |
|---|---|---|---|
| 6,511,427 | B1 | 1/2003 | Sliwa, Jr. et al. |
| 6,770,033 | B1 | 8/2004 | Fink |
| 7,444,875 | B1 * | 11/2008 | Wu .......................... A61B 8/08 600/438 |
| 7,578,789 | B2 * | 8/2009 | Sandrin ................ A61B 5/0048 600/438 |
| 7,785,259 | B2 | 8/2010 | Zheng et al. |
| 8,602,994 | B2 | 12/2013 | Zheng et al. |
| 8,734,350 | B2 | 5/2014 | Greenleaf et al. |
| 2004/0225215 | A1 | 11/2004 | Querleux |
| 2005/0119568 | A1 * | 6/2005 | Salcudean ................ A61B 8/08 600/437 |
| 2011/0201931 | A1 | 8/2011 | Palmeri et al. |
| 2012/0123262 | A1 * | 5/2012 | Xie ...................... A61B 5/0048 600/438 |
| 2012/0215101 | A1 * | 8/2012 | Maleke .................. A61B 5/055 600/438 |
| 2012/0269414 | A1 | 10/2012 | Zha et al. |
| 2014/0147012 | A1 | 5/2014 | Shandas et al. |
| 2014/0147013 | A1 | 5/2014 | Shandas et al. |
| 2014/0330122 | A1 † | 11/2014 | Baghani |

FOREIGN PATENT DOCUMENTS

| | | |
|---|---|---|
| JP | H08191834 | 7/1993 |
| JP | 2008539005 | 11/2008 |
| WO | 2009/140607 | 11/2009 |
| WO | 2012/080913 | 6/2012 |
| WO | 2012080913 A1 | 6/2012 |
| WO | 2013/026141 | 2/2013 |
| WO | 2013160468 | 10/2013 |
| WO | 2014/055973 | 4/2014 |
| WO | 2014128182 | 8/2014 |

OTHER PUBLICATIONS

International Search Report and Written Opinion dated Jan. 19, 2016 in connection with PCT/US2015/057825.
Extended European Search Report from related EP Publication No. 3215018, dated Aug. 9, 2018, 10 pages.
Parajuli, RK, et al. "Shear wave imaging using phase modulation component of harmonic distortion in continuous shear wave excitation." Japanese Journal of Applied Physics 52.7S (2013): 07HF22.
China National Intellectual Property Administration, First Office Action for application 201580059146.6, dated Jul. 3, 2019, with associate translation.
Japan Patent Office, Japanese Office Action for application 2017-523369, dated Jul. 2, 2019, with associate translation.
Schiro, A Research Platform for Ultrasonic Elastography Based Prostate Biopsy, Master's Thesis, Nov. 30, 2013, Vancouver.†
Eskandari, Identifying Malignant and Benign Breast Lesions Using Vibroelastography, 2013.†

* cited by examiner
† cited by third party

METHOD FOR ULTRASOUND ELASTOGRAPHY THROUGH CONTINUOUS VIBRATION OF AN ULTRASOUND TRANSDUCER

CROSS-REFERENCE TO RELATED APPLICATIONS

This application represents the national stage entry of PCI International Application No, PCT/2015/057825 filed on Oct. 28, 2015, which claims the benefit of U.S. Provisional Patent Application Ser. No. 62/072,167, filed on Oct. 29, 2014, both which are incorporated herein by reference as if set forth in their entirety.

STATEMENT REGARDING FEDERALLY SPONSORED RESEARCH

This invention was made with government support under DK082408 awarded by the National Institutes of Health. The government has certain rights in the invention.

BACKGROUND OF THE INVENTION

The present invention relates to the determination of mechanical properties of tissues through ultrasound elastography. More specifically, the invention relates to an elastography method that utilizes continuous vibration of an ultrasound transducer.

Mechanical properties of tissue such as elasticity and stiffness are closely associated with the state of tissue health. For example, fibrotic and cancerous tissues often have a higher stiffness than that of healthy tissues. Therefore, elastography methods that can noninvasively measure tissue mechanical properties have great medical applications such as liver fibrosis staging and cancer diagnosis.

Shear waves can be introduced in tissue and the shear wave propagation parameters can be measured and used to estimate tissue mechanical properties quantitatively. These parameters can include group propagation speed, attenuation, shear modulus, shear viscosity, storage modulus, loss modulus, Young's modulus, and mechanical relaxation time, and frequency dependent propagation parameters.

A current elastography method requires an ultrasound radiation force from a focused or unfocused ultrasound "push" beam with long duration, typically hundreds of microseconds, to produce shear waves in tissue for quantitative measurements of tissue mechanical properties. However, the shear waves generated by ultrasound radiation force are typically very weak, limiting the penetration depth of these methods. In addition, the push beam requires transmission of hundreds of ultrasound cycles at high voltage, which is very demanding on the transmit circuit of the ultrasound scanner and the transducer.

As a result, this method is limited to high end ultrasound scanners with large capacity transmit circuits that can support the transmission of push beams. In addition, the updating frequency for continuous measurement is very low, typically below 1 Hz, compared to real-time B-mode imaging, to prevent excessive heating to tissue or ultrasound transducer. This low updating frequency makes it difficult to find lesions with abnormal stiffness by just using the shear wave imaging, as some lesions may appear to be healthy tissue in B-mode imaging.

It is also possible for shear waves in tissue to be generated by external mechanical vibration. For example, in a transient elastography device commercially marketed as Fibroscan® (Echosens; Paris, France), an ultrasound transducer is vibrated by a mechanical actuator with a transient "punch," which can produce a transient shear wave that propagates away from the transducer into the nearby tissue. This shear wave can be detected by the same ultrasound transducer in pulse-echo mode for stiffness quantification.

However, the Fibroscan® device is unable to make 2D elastography images and cannot provide real-time B-mode imaging as scan guidance. Also the Fibroscan® device cannot continuously update its elastography measurements. Rather, the acquisition sequence has to be activated again with a button push by the user to produce another transient shear wave for the new measurement.

Continuous vibration can produce continuous shear waves in tissue so that shear waves are present in tissue at all times. This approach can potentially facilitate continuous updating of elastography measurements, which, for example, can be useful for capturing transient changes in the stiffness of a muscle during contraction. In one system featuring continuous vibration, a handheld vibrator is positioned adjacent to an ultrasound transducer to generate continuous vibration and shear waves that are measured by the transducer. Although this system is feasible, this approach requires the operator to use both hands, one to hold the vibrator and one to hold the transducer. This requirement greatly limits the clinical value of this system, as in typical clinical practice, a single sonographer will use one hand to maneuver the ultrasound transducer and the other hand to control the ultrasound scanner while scanning a patient.

In an additional system, crawling waves produced from two vibration sources with different frequencies positioned at two sides of the ultrasound transducer have been used for elastography measurements. This method also requires extra fixtures to hold the two vibration sources in contact with the tested object and therefore is not convenient for clinical practice.

Accordingly, it would be desirable to have a system capable of inducing continuous mechanical vibrations to the tissues that does not require the user to exercise both hands during operation.

SUMMARY OF THE INVENTION

The present invention overcomes the aforementioned drawbacks by teaching a method for ultrasound elastography that induces continuous mechanical vibration through the ultrasound transducer into the object being imaged.

In accordance with one aspect of the invention, a method for measuring a mechanical property of an object using an ultrasound system having a transducer is provided. The method includes providing a continuous vibration to the transducer using at least one actuator coupled to the transducer. At least one shear wave is induced in the object by the continuous vibration of the transducer. Shear wave data sets are obtained from the object using the transducer, and motion-corrected shear wave data sets are produced by correcting the shear wave data sets to remove motion artifacts associated with the continuous vibration of the transducer. The motion-corrected shear wave data sets are then processed to calculate a mechanical property of the object.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full

DETAILED DESCRIPTION

This disclosure provides a system and a method for distinguishing the mechanical properties of tissue through ultrasound elastography, in which shear waves are generated in a subject using continuous vibration of the ultrasound transducer. Several methods for removing motion artifacts caused by the continuous vibration of the ultrasound transducer are also provided.

Figure 1:
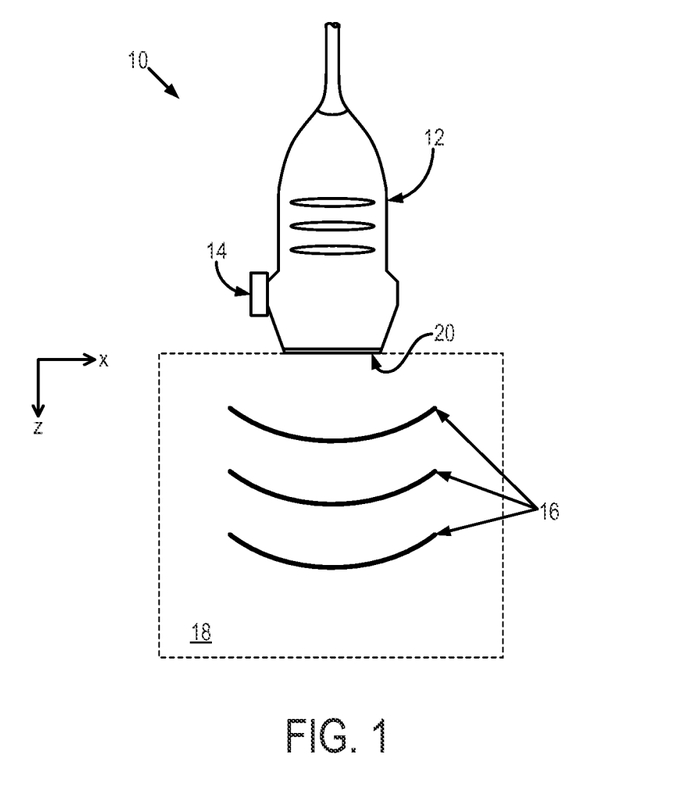
FIG. 1 is a block diagram of an example ultrasound system that implements a continuous vibration of the ultrasound transducer to induce shear waves in an object.

Referring first to FIG. 1, an example system 10 for inducing shear waves in an object 20 is illustrated. In this system, the transducer 12 is mechanically vibrated by an actuator 14, which causes the transducer 12 to oscillate in the axial direction (e.g., the z-direction in FIG. 1). As one example, the actuator 14 can be a mechanical actuator, such as a voice coil actuator. As the transducer 12 moves in the axial direction, shear waves 16 are induced within the object 18. Shear waves 16 can also be produced from mode conversion of compressional waves. The produced shear waves 16 are then detected by the same ultrasound transducer 12 operating in a pulse-echo mode to provide quantitative measurements of mechanical properties of the object.

The actuator 14 is coupled to the ultrasound transducer 12. As one example, the actuator 14 can be attached directly to the outer surface of the transducer 12. For illustration purposes, the actuator 14 is attached to one side of transducer 12 in FIG. 1. In some applications, however, it may be preferred to align the actuator co-axially with the transducer 12 so that the transducer motion is primarily axial with minimal transverse and azimuthal motions. This setup eliminates the need for a separate vibration source, and therefore allows for a convenient single-handed operation. The vibration is preferably continuous to allow continuous updating of measurements.

The ultrasound transducer 12 can be vibrated axially along the beam axis of ultrasound, or in other directions depending on the desired imaging application. The ultrasound system used for shear wave detection can be operated to detect a single A-line, multiple A-lines through parallel beam forming, or an entire 2D area or 3D volume with plane wave imaging and software beam forming, such as is done in a Verasonics® ultrasound scanner.

The continuous vibration applied to the ultrasound transducer 12 by the actuator 14 can contain multiple frequencies, and the detected shear waves can thus be processed to resolve frequency dependent properties of the object. For example, the processing may use a bandpass filter along the time dimension to select only one frequency at a time, and the subsequent processing would be identical to that as if data were collected with a single vibration frequency. Multi-frequency vibrations can speed up acquisition for dispersion analysis. With continuous vibration and continuous shear wave detection and processing, elastography measurements can be updated continuously in a substantially real-time manner.

When the transducer 12 is vibrating in the axial direction, such as when the vibration is normal to the active surface 20 of the transducer 12, the motion of the transducer 12 will contaminate the shear wave signals detected in the object 18. This signal contamination is present because ultrasound motion detection uses the transducer 12 as a non-moving reference coordinate, but this assumption is violated when the transducer 12 is oscillating due to external vibration. Therefore, motion of the transducer 12 that is caused by the actuator 14 needs to be corrected for in order to properly measure mechanical properties from the detected shear waves.

Figure 2:
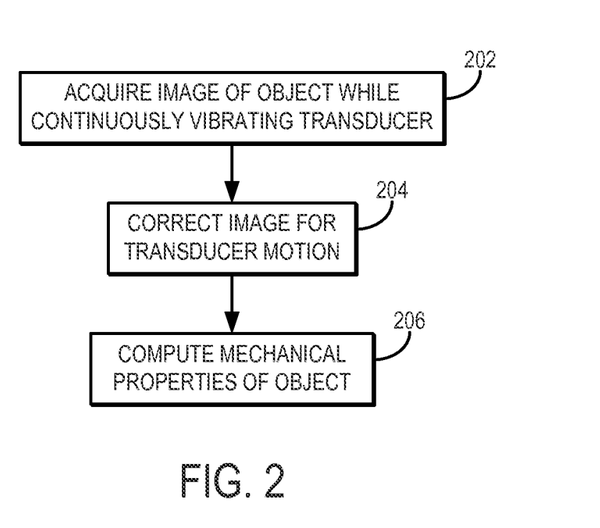
FIG. 2 is a flowchart setting forth the steps of an example method for acquiring shear wave data using an ultrasound transducer that is continuously vibrating, and for correcting those data for effects of the continuously vibration motion of the transducer.

Referring to FIG. 2, an example method for ultrasound elastography using continuous vibration of the ultrasound transducer as the motion source for generating shear waves is given. The method includes acquiring images of a subject with an ultrasound system while applying continuous vibration to the subject by continuously vibrating the transducer, as indicated at step 202. Following the acquisition of the image, it is desirable to process the acquired images to compensate for the motion of the transducer, as detailed in step 204. Several methods to remove this transducer motion artifact are discussed below. Following the correction of the image, mechanical properties of the subject being imaged are computed, as indicated in step 206. Examples of mechanical properties that can be computed include shear wave speed, shear wave attenuation, shear modulus, shear viscosity, storage modulus, loss modulus, Young's modulus, mechanical relaxation time, and dispersion.

Figure 3:
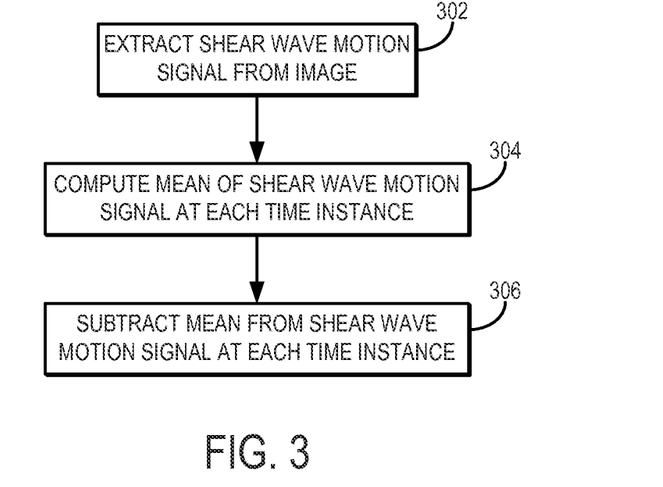
FIG. 3 is a flowchart setting forth the steps of an example of a method for correcting motion-corrupted shear wave data using a subtraction of the mean technique.

Following the initial acquisition of an image of the object, it has been stated that this image must be corrected for transducer motion. Referring to FIG. 3, one example method of correcting for the transducer motion first requires the extraction of the shear motion signal from the acquired image, as indicated at step 302. The mean of the shear wave motion signal is then computed, as indicated at step 304. The mean shear wave motion is then subtracted from the shear wave motion signal at all time instances to create a corrected image, as indicated at step 306.

In one example of this method, a one-dimensional (1D) array transducer is vibrating at 100 Hz. The motion of the transducer will add a 100 Hz signal to all shear waves detected, at all pixels within the two-dimensional imaging plane. At any given time, the transducer motion is a uniform offset value applied to these pixels.

Therefore, transducer motion at a given time instance may be mitigated by subtracting the mean of shear wave motion, detected at that time instance, from every pixel within the entire 2D imaging area. This type of processing can be repeated at all time instances during the course of imaging to fully suppress the transducer motion artifact.

This method assumes that shear wave length is small relative to the size of the 2D imaging area. This assumption allows for the additional assumption that the true shear wave motion not contaminated transducer motion has a zero value within the 2D imaging area.

Figure 4:
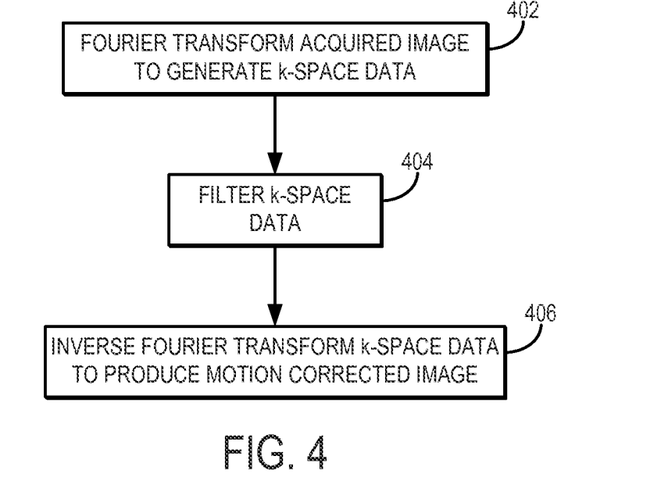
FIG. 4 is a flowchart setting forth the steps of an example of a method for correcting motion-corrupted shear wave data using a k-space filtering technique.

Another method for suppressing transducer motion interference utilizes k-space filtering. Referring to FIG. 4, a flowchart setting forth the steps for an example of such a method is illustrated. After acquiring the initial image, the image undergoes Fourier transformation to generate a set of k-space data, as indicated at step 402. This k-space data is then filtered to suppress unwanted data, as indicated at step 404. The filtered k-space data is then converted to a motion-corrected image by applying an inverse Fourier transform, as indicated at step 406.

Figure 5:
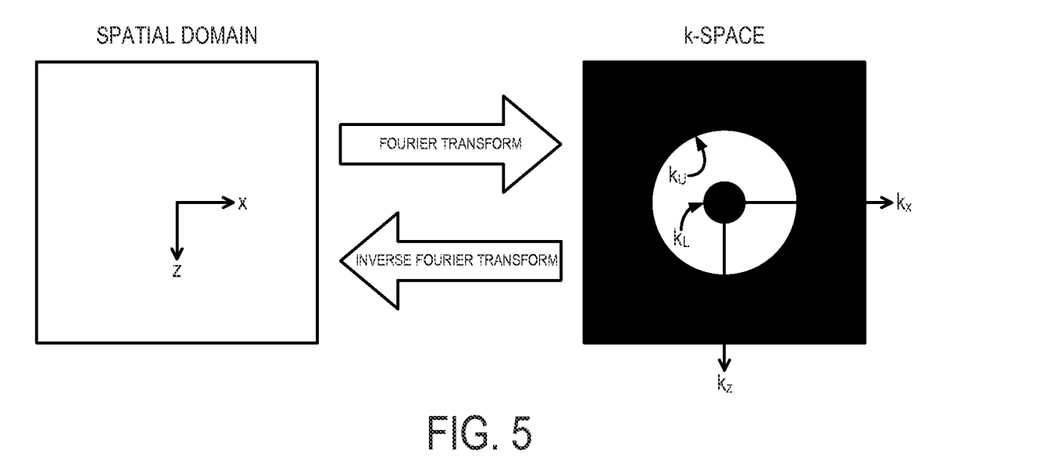
FIG. 5 is a graphic representation of an example k-space filtering technique.

An example of this method is described with reference to FIG. 5. Using the same 1D transducer example as described in the previous method, the detected shear wave motion at any given time instance can be considered to be a 2D image u(x, z) in the spatial domain. Thus, an image is acquired with an ultrasound transducer while the transducer is being continuously vibrated, as indicated at step 202 of FIG. 2. In this image, u is a tissue motion, which may include displacement, velocity, or acceleration of the tissue in response to the continuous vibration of the transducer. A Fourier transformation is then applied to convert the image from the spatial domain to a frequency domain. By way of example, the Fourier transform along the two spatial dimensions of u(x, z) produces a frequency domain, or k-space, representation of the motion, $U(k_x, k_z)$. For a given pixel in k-space with coordinate $(k_x, k_z)$, the distance to the origin of k-space $k_r = \sqrt{k_x^2 + k_z^2}$ represents the spatial frequency of that pixel. Transducer motion has very large spatial features in the spatial (x, z) domain, and therefore will be represented by pixels with very small $k_r$ values.

The k-space data is then filtered by setting an upper and lower limit of $k_r$ to provide a data set free of noise caused by the transducer. By way of example, the k-space data can be filtered as follows. A lower limit of $k_l$ can be set such that all pixels with $k_r < k_l$ are set to zero. Using black pixels to represent pixels set to zero, this process is illustrated by the small black disk in FIG. 5. Similarly, an upper limit of $k_u$ can be set such that all pixels with $k_r > k_u$ are set to zero, illustrated by the black area outside the white donut. This process is very useful to suppress "salt-and-pepper" noise in the u(x, z) caused by ultrasound speckles.

In effect, applying the $k_l$ and $k_u$ limits bandpass filters the k-space data. A smooth transition instead of a step function can be applied at these limits to reduce Gibbs ringing effects. With the upper and lower limits applied to define a filter, a filtered data set is created. An inverse Fourier transform can then be applied on the filtered data to transform the data back to the (x, z) spatial domain. The new, corrected image provides the desired elastography reading, with transducer motion and shear wave speckle noise both being suppressed.

In this method, if the temporal frequency of the continuous vibration is f, the k-space bandpass filtering is essentially applying speed limits on the shear wave data such that shear waves with speed lower than $f/k_u$ or higher than $f/k_l$ are suppressed. Since the biological range of the shear wave speed is usually known for different tissues, this can help one select the proper $k_l$ and $k_u$ limits.

Figure 6:
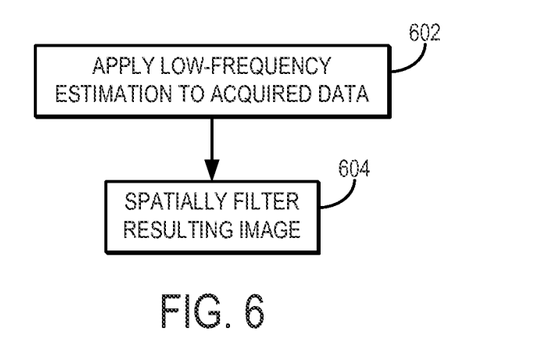
FIG. 6 is a flowchart setting forth the steps of an example of a method for correcting motion-corrupted shear wave data using a low-frequency estimation technique.

Referring now to FIG. 6, a flowchart is illustrated as showing the steps for another example method for correcting for transducer motion, in which local frequency estimation (LFE) is used. Local frequency estimation is a method widely used in magnetic resonance elastography ("MRE") to estimate the local wave length of single frequency harmonic shear waves for calculation of the propagation speed of shear waves. After acquisition of the image in step 202 of FIG. 2, LFE is applied to the image as indicated at step 602, and the resulting image can be spatially filtered to suppress noise still present in the image, as indicated at step 604.

For example, when applied on a 2D shear wave motion image at a given time instance, the LFE can track the local image gradient to estimate local shear wave wavelength. Therefore, the LFE is immune to uniform background offset of the 2D shear wave image due to transducer motion.

As a result, LFE can give correct shear wave speed estimations when the input shear wave data are contaminated by transducer motion. However, LFE is sensitive to speckle noise in the shear wave data and may give decreased shear wave length. Thus, an underestimate of the shear wave speed is provided when the data have speckle noise. Therefore, the k-space filtering or other smoothing methods in the spatial (x, z) domain such as Gaussian smoothing spatial filter can be used to suppress the speckle noise before LFE processing is performed.

Figure 7:
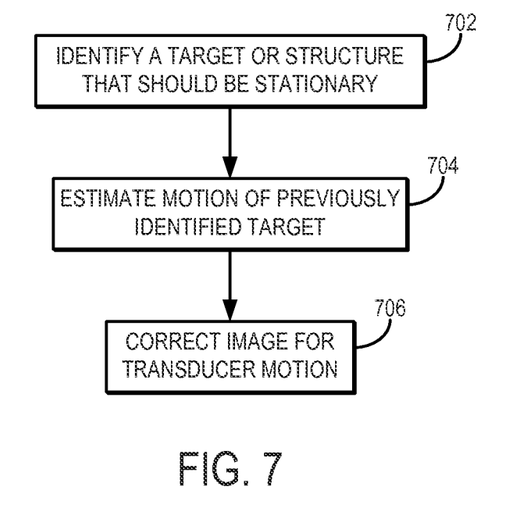
FIG. 7 is a flowchart setting forth the steps of an example of a method for correcting motion-corrupted shear wave data using a technique that estimates the transducer motion from a normally stationary target.

A flowchart showing the process flow of another example method for suppressing transducer motion is shown in FIG. 7. In this method, a target or structure that is known to be substantially stationary is identified within the initial image, as indicated at step 702. As an example, the stationary target or structure can be an anatomical target or structure, such as a bone that is known to be substantially stationary. Following acquisition of the image, an estimate of the motion of the normally stationary target or structure is made, as indicated at step 704.

Because the identified target is normally stationary, the estimate of its motion can be used as an estimate for the motion induced by the continuously vibrating transducer. Correcting for the motion of the transducer can thus be made based on the estimate of the identified target's motion. When the shear wave imaging region includes targets that are known to be stationary or not moving, such as bone, motion at these targets seen by the ultrasound transducer is known to be caused by vibration of the transducer. Therefore, motion at such targets can be subtracted from motions at all pixels to correct for transducer motion, as indicated at step 706.

In another example method for eliminating transducer motion from the image, a spatial gradient is applied to the acquired image. A spatial gradient operation can be applied to the 1D, 2D, or 3D spatial shear wave data at a given time instance to remove transducer motion. Transducer motion is known to be relatively uniform across all spatial dimensions, and will therefore be suppressed by the spatial gradient operation.

In addition to transducer motion, a continuous vibration may also generate standing wave patterns that may be undesirable for various applications. Directional filtering can be utilized to separate the shear waves into unidirectional waves. These unidirectional waves can then be processed by LFE or time-of-flight methods for shear wave speed estimation. In addition, direct inversion can also be used to calculate tissue mechanical properties from the shear wave field processed by k-space filtering or directional filtering.

In some embodiments, the images acquired in step 202 are acquired while implementing rapid sampling of the shear wave field by pulse-echo ultrasound. In the following example, 2D spatial shear wave detection is utilized; however, it should be understood that the methods taught in this disclosure can be readily extended to three dimensions in space.

As one example of rapid sampling, a harmonic shear wave is sampled over a 2D region at many times the vibration frequency of the shear wave. For instance, a harmonic shear wave can be sampled at 10 times its vibration frequency, which may be 50 Hz or the like. High-end, conventional ultrasound imaging systems can image several A-lines from a single transmission using parallel beam forming.

Figure 8:
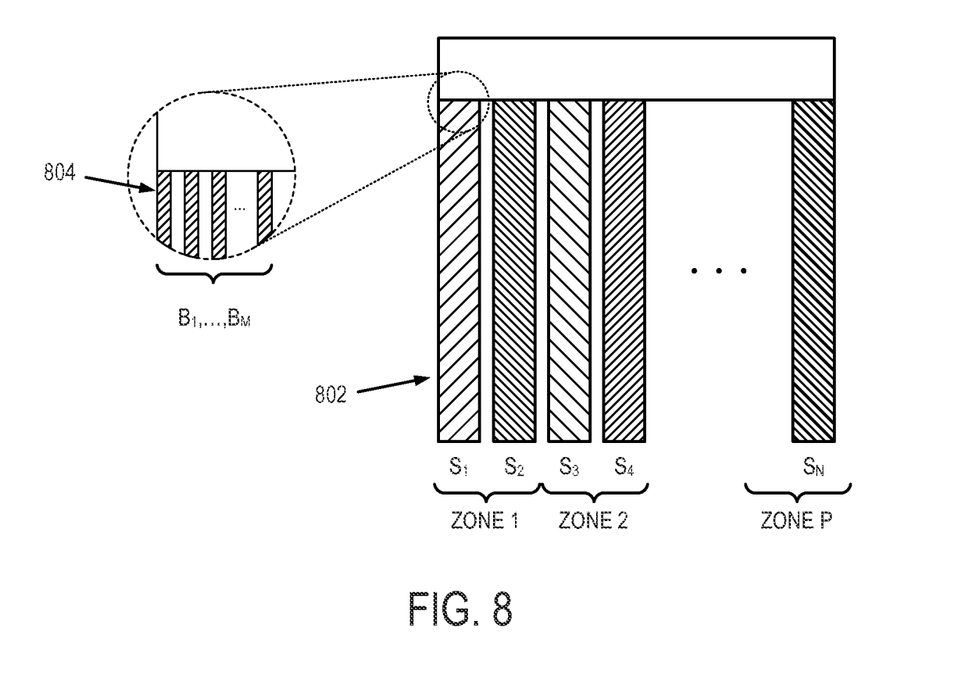
FIG. 8 is an example of a plurality of different ultrasound beam sets.

As shown in FIG. 8, N sets of ultrasound beams {S1, . . . , SN} 802, each of M beams {B1, . . . , BM} 804, are formed in parallel. The beam sets 802 are used to cover the entire 2D region being imaged. Assume that the beam sets 802 are sequentially detected {S1, . . . , SN} at a pulse repetition frequency (PRF) of 10 kHz. This process can be repeated at a frequency of 10 kHz/N. Therefore, an N of 20 will allow an effective sampling frequency of 500 Hz at each beam location.

Figure 9:
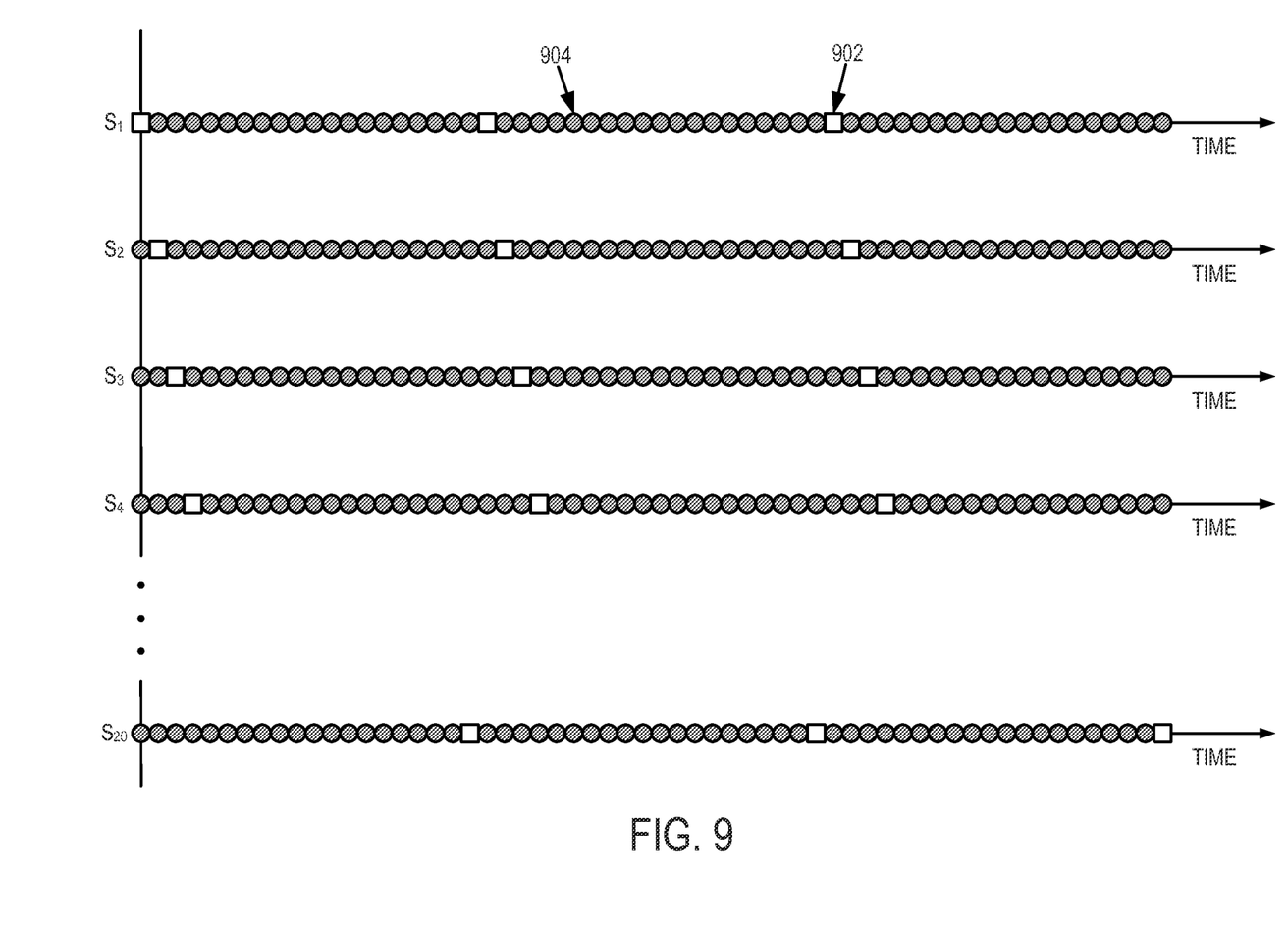
FIG. 9 is a diagram illustrating an example timing of ultrasound beam sets.

As shown in FIG. 9, the squares 902 represent the time instances of ultrasound detection at locations covered by beam sets S1 to SN. Each beam set is sampled at a PRF of 500 Hz, but there is a time shift of 100 microseconds between adjacent beam sets. This small time delay among different beam sets needs to be accounted for in shear wave elastography reconstruction. There are several ways to correct for this delay problem, which are discussed below.

In one example method of correcting for the time delay between beam sets, a time interpolation is applied. For example, with time interpolation assigned to 10 kHz, the time grids for each beam can be aligned and synchronized. The interpolated points are represented by filled circles 904 in FIG. 9. Shear waves produced by continuous vibration at a single frequency provide essentially a cyclic sine wave versus time at each pixel.

In another example method for correcting for the time delay between beam sets, the shear waves are shifted so as to provide a set of waves with equivalent sine cycles. When the 2D area to be imaged is large, the effective sampling frequency at each pixel PRF/N is too slow if all beam sets of the 2D area are sampled in one sequential detection as described above. To solve this problem, the beam sets can be divided into multiple zones, as shown in FIG. 8, and each zone can be detected with the approach described above at sufficiently high effective sampling frequencies.

Figure 10:
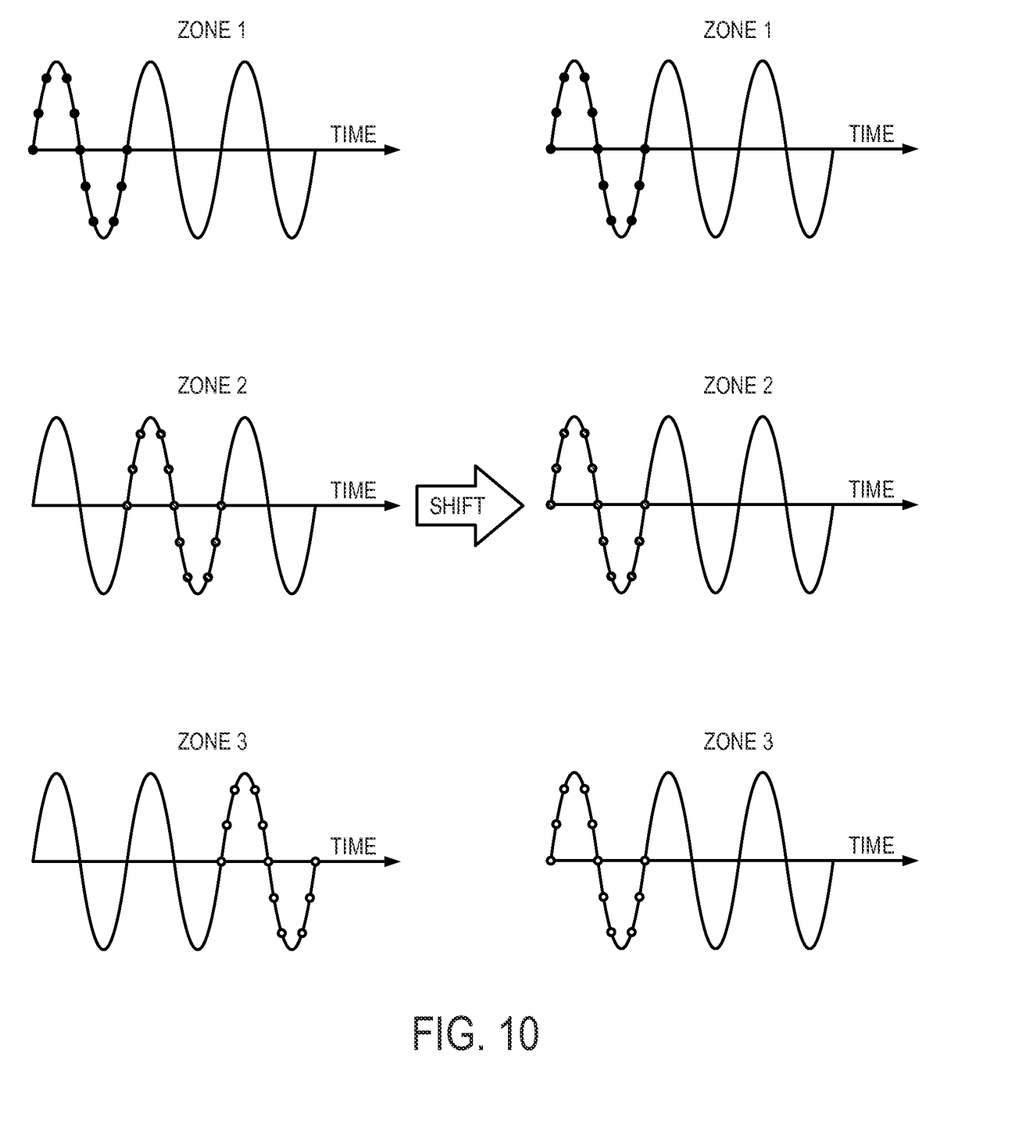
FIG. 10 is an example illustration of shifting shear waves originally at different sine cycles to equivalent sine cycles.

To provide effective sampling, the zones can be sequentially imaged one zone at a time. Referring to FIG. 10, zone 1 is detected over the first sine cycle, in which black circles represent the detection time instances; zone 2 is detected over the second sine cycle, in which gray circles represent the detection time instances; and zone 3 is detected over the third sine cycle, in which white circles represent the detection time instances. Because the shear wave signal is sinusoidal and cyclic, the signals at zone 2 and zone 3 can be shifted to the same sine cycle as zone 1.

Through this process, shear wave signals for all zones have been generated that are aligned and have a high effective sampling frequency. Alternatively, one big zone can be used to cover the entire 2D imaged area, and shear waves detected at all beam sets can be shifted to the same sine cycle to gain an effective sampling frequency higher than that which is present without shifting. It should be noted that the shifting methods taught here can only shift integer number of whole sine wave cycles. The time interpolation method taught above can be further used for additional alignment within the same sine cycles.

In an additional example method of correcting for the time delay between beam sets, the shear sine wave signals are parametrically fit to a common time grid. Referring again to the left side of FIG. 10, it should be noted that the actual time which individual beam sets are sampled can scatter over different sine cycles. Because the frequency of the sine wave and the actual timing of the samples are known, the sine wave can be fit to the samples and estimation of the amplitude and phase of the sine wave at each beam can be performed.

Following this estimation, the motion at any time can be calculated from the sine wave model using the estimated amplitude and phase parameter. In this process, time grids of all beams can be aligned to a common time grid. This approach proves to be flexible, as the original sampled time points for each beam set can be non-uniformly spaced and may be scattered over multiple cycles with gaps between individual time points.

The above teaching uses 1D array transducer and 2D shear wave detection as examples for illustration. It should be noted that the methods can be applied to single element transducers, 1D array transducers, 2D mechanical scanning transducers, and 2D array transducers with 1D, 2D, and 3D shear wave detection capabilities.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for measuring a mechanical property of an object using an ultrasound system having a transducer, the steps of the method comprising:
   a) continuously vibrating the transducer over an acquisition sequence using at least one actuator attached to the transducer;
   b) inducing at least one shear wave in the object by the continuous vibration of the transducer;
   c) obtaining and continuously updating shear wave data sets from the object using the transducer while the transducer is being continuously vibrated;
   d) after obtaining the shear wave data sets, producing motion-corrected shear wave data sets by correcting the shear wave data sets to remove motion artifacts associated with the continuous vibration of the transducer; and
   e) processing the motion-corrected shear wave data sets to calculate a mechanical property of the object;
   wherein step d) further includes the steps of applying a Fourier transform to the shear wave data sets to generate k-space data sets, filtering the k-space data, and applying an inverse Fourier transform to the filtered k-space data sets to produce the motion corrected shear wave data sets; and
   wherein filtering the k-space data sets includes applying a bandpass filter to the k-space data sets.

2. The method of claim 1, wherein the mechanical property of the object being calculated in step e) includes at least one of shear wave speed, shear wave attenuation, shear modulus, shear viscosity, storage modulus, loss modulus, Young's modulus, mechanical relaxation time, and dispersion.

3. The method of claim 1, wherein step d) further includes the steps of extracting a shear wave motion signal from the shear wave data sets, computing a mean of the shear wave motion signal at a time instance, and subtracting the mean from the shear wave motion signal at all other time instances.

4. The method of claim 1, wherein step d) includes producing the motion-corrected shear wave data sets by applying a local-frequency estimation to the acquired shear wave data sets.

5. The method of claim 1, wherein step d) further includes the steps of identifying a normally stationary target in the shear wave data sets, estimating a motion of the normally stationary target, and subtracting the estimated motion of the normally stationary target from the shear wave data sets.

6. The method of claim 1, wherein step d) includes producing the motion-corrected shear wave data sets by applying a spatial gradient to the shear wave data sets.

7. The method of claim 1, wherein the actuator of step a) is a voice coil actuator.

8. The method of claim 1, wherein step c) includes sampling the at least one induced shear wave using pulse-echo ultrasound with a sampling rate that is greater than a vibration frequency of the at least one induced shear wave.

9. The method of claim 8, wherein the obtained shear wave data sets are corrected for a time delay between shear wave data sets.

10. The method of claim 9, wherein the correction for the time delay includes applying a time interpolation to the shear wave data sets.

11. The method of claim 9, wherein the correction for the time delay includes shifting the shear wave data sets to have equivalent sine wave cycles.

12. The method of claim 9, wherein the correction for the time delay includes parametrically fitting the shear wave data sets to a common time grid.

13. The method of claim 1, wherein the continuous vibration provided to the transducer contains multiple frequencies, and step e) includes processing the shear wave data sets to resolve frequency dependent properties of the object.

14. The method of claim 13, wherein step e) includes using a bandpass filter along a time dimension to select at least one of the multiple frequencies of the continuous vibration for which mechanical properties are calculated.

* * * * *